US010393502B2

(12) United States Patent
Johnson et al.

(10) Patent No.: US 10,393,502 B2
(45) Date of Patent: Aug. 27, 2019

(54) REAL TIME FPGA RESAMPLING FOR SWEPT SOURCE OPTICAL COHERENCE TOMOGRAPHY

(71) Applicant: Axsun Technologies LLC, Billerica, MA (US)

(72) Inventors: Bartley C. Johnson, North Andover, MA (US); Noble G. Larson, Arlington, MA (US); Brian Goldberg, Cambridge, MA (US); Mark E. Kuznetsov, Lexington, MA (US)

(73) Assignee: AXSUN TECHNOLOGIES, INC., Billerica, MA (US)

( * ) Notice: Subject to any disclaimer, the term of this patent is extended or adjusted under 35 U.S.C. 154(b) by 607 days.

(21) Appl. No.: 14/809,747

(22) Filed: Jul. 27, 2015

(65) Prior Publication Data

US 2016/0025478 A1    Jan. 28, 2016

Related U.S. Application Data

(60) Provisional application No. 62/029,003, filed on Jul. 25, 2014.

(51) Int. Cl.
*G01B 9/02* (2006.01)
*A61B 5/00* (2006.01)

(52) U.S. Cl.
CPC ........ *G01B 9/02067* (2013.01); *A61B 5/0066* (2013.01); *G01B 9/02004* (2013.01); *G01B 9/02041* (2013.01); *G01B 9/02083* (2013.01); *G01B 9/02091* (2013.01)

(58) Field of Classification Search
CPC .......................... G01B 9/02067; A61B 5/0066

USPC .......................................................... 702/191
See application file for complete search history.

(56) References Cited

U.S. PATENT DOCUMENTS

| 7,415,049 | B2 | 8/2008 | Flanders et al. |
| 8,526,472 | B2 | 9/2013 | Flanders et al. |
| 8,564,783 | B2 | 10/2013 | Flanders et al. |
| 2009/0290167 | A1 | 11/2009 | Flanders et al. |
| 2011/0080591 | A1 | 4/2011 | Johnson et al. |
| 2013/0271772 | A1* | 10/2013 | Johnson ............. G01B 9/02004 356/479 |
| 2014/0207418 | A1 | 7/2014 | Vemishetty |

(Continued)

OTHER PUBLICATIONS

International Preliminary Report on Patentability and Written Opinion of the International Searching Authority, dated Jan. 31, 2017, from International Application No. PCT/US2015/042236, filed Jul. 27, 2015. Seven pages.

(Continued)

*Primary Examiner* — Ricky Ngon
(74) *Attorney, Agent, or Firm* — HoustonHogle LLP

(57) ABSTRACT

Real-time swept source OCT data is most often sampled using a specially cut hardware k-clock. The present invention involves mathematically resampling signals within an FPGA-based data acquisition board based on data sampled from a wide free spectral range reference interferometer. The FPGA can then multiply up the reference clock rate to achieve greater imaging depth. The Nyquist fold-over depth can thus be programmed from a standard reference to an arbitrary depth, much as PLL frequency synthesizer can produce many frequencies from a standard stable reference. The system is also capable of real-time performance.

31 Claims, 15 Drawing Sheets

(56) References Cited

U.S. PATENT DOCUMENTS

| | | | |
|---|---|---|---|
| 2014/0268166 A1* | 9/2014 | Flanders | G01B 9/02004 356/479 |
| 2015/0184995 A1 | 7/2015 | Goldberg et al. | |
| 2015/0300806 A1* | 10/2015 | Goldberg | G01B 9/02083 356/479 |

OTHER PUBLICATIONS

"12-bit High-Speed PCIe ADS Card Available with Optical Coherence Tomography Technology," Benedetta Viti, Jan. 27, 2015. Downloaded from high-speed-digitizer.blogs.keysight.com/data-acquisition-for-oct. Keysight Technologies. One page.

"ADQI4OCT—Data Acquisition Unit—Digitizer: 14-bit, 1 GHz Swept-Source Optical Coherence Tomography platform—PCI Express & USB 3," Downloaded from https://www.spdevices.com/index.php/adqu14oct. 2004-2017, Teledyne Signal Processing Devices Sweden AB. Five pages.

"ADQ14OCT—datasheet." Downloaded from www.spdevices.com. 2015, Signal Processing Devices Sweden AB. Eleven pages.

Hsu, K. et al., "Miniature, Fast Wavelength-Swept Sources Based on External Grating Cavity with Resonant MEMS Mirror," paper presented at Conference on Lasers and Electro-Optics, Jun. 10, 2013. Exalos AG. Forty-two pages.

Bandi et al., FPGA-Based Real-Time Swept-Source OCT Systems for B-Scan Live-Streaming or Volumetric Imaging. Proceeding of SPIE, vol. 8571, Mar. 20, 2013, p. 85712Z.

Desjardins et al., Real-Time FPGA Processing for High-Speed Optical Frequency Domain Imaging. IEEE Transactions on Medical Imaging, vol. 28, No. 9, Aug. 26 2009, pp. 1468-1472.

International Search Report and Written Opinion, PCT/US2015/042236, dated Oct. 20, 2015.

Bandi et al., "FPGA-Based Real-Time Swept-Source OCT Systems for B-Scan Live-Streaming or Volumetric Imaging," Proceedings of SPIE 8571, Optical Coherence Tomography and Coherence Domain Optical Methods in Biomedicine XVII, 8571Z (6 pages), 2013.

Choma et al., "Swept Source Optical Coherence Tomography Using an All-Fiber 1300-nm Ring Laser Source," Journal of Biomedical Optics 10 (4): 4400, 2005.

Desjardins et al., "Real-Time FPGA Processing for High-Speed Optical Frequency Domain Imaging," IEEE Transactions on Medical Imaging 28 (9): 1468-72, 2009.

Laakso et al., "Splitting the Unit Delay—Tools for Fractional Delay Filter Design," IEEE Signal Processing Magazine 13:30-60, 1996.

Li et al., "Scalable, High Performance Fourier Domain Optical Coherence Tomography: Why FPGAs and Not GPGUs," Proceedings of the 2011 IEEE 19th Annual International Symposium on Field-Programmable Custom Computing Machines, FCCM 11, 2011.

Vakoc et al., "Phase-Resolved Optical Frequency Domain Imaging," Optics Express 13 (14): 5483-93, 2005.

Zhang and Kang, "Graphics Processing Unit Accelerated Non-Uniform Fast Fourier Transform for Ultrahigh-Speed, Real-Time Fourier-Domain OCT," Optics Express 18 (22): 23472-87, 2010.

* cited by examiner

| Parameter | Min | Value | Max | Units |
|---|---|---|---|---|
| Maximum scan depth in air | | 3.500 | | mm |
| Length of air clock etalon | | 7.0 | | mm |
| FSR of clock etalon | | 21.4 | | GHz |
| Sweep Frequency | | 100 | | kHz |
| Wavelength Range | 993.0 | | 1103.0 | nm |
| Optical Frequency Range | 271.797 | | 301.906 | THz |
| Data Range in wavelength | 998.6 | | 1096.2 | nm |
| Data Range in optical frequency | 273.479 | | 300.224 | THz |
| Sweep Range | | 110.0 | | nm |
| Sampled Range | | 97.7 | | nm |
| Maximum Samples | | 1406 | | |
| Percent bandwidth used | | 89 | | % |
| Selected number of samples | | 1250 | | |
| Pixels in A-scan | | 625 | | |
| Duty Cycle | | 44 | | % |
| Estimated Clock Frequency | | 284 | | MHz |
| 3 dB Resolution for Hann Window | | 8.1 | | μm |
| 10 dB Resolution for Hann Window | | 14.1 | | μm |
| 20 dB Resolution for Hann Window | | 18.6 | | μm |

FIG. 8

REAL TIME FPGA RESAMPLING FOR SWEPT SOURCE OPTICAL COHERENCE TOMOGRAPHY

CROSS-REFERENCE TO RELATED APPLICATION

This application claims priority to and the benefit of U.S. Provisional Application 62/029,003, filed Jul. 25, 2014, the contents of which are incorporated herein by reference in their entirety.

FIELD OF THE INVENTION

The invention generally relates to optical coherence tomography, and particularly to resampling of interference signals.

BACKGROUND

Optical coherence analysis and specifically optical coherence tomography ("OCT") are important medical imaging tools that use light to capture three-dimensional images in micrometer-resolution non-invasively from the sub-surface of a sample, such as a biological tissue. OCT is useful for such applications as industrial inspection and in vivo analysis of biological tissues and organs.

A common OCT technique is Fourier domain OCT ("FD-OCT"), of which there are generally two types: Spectral Domain OCT and Swept Source OCT. In both systems, optical waves are reflected from an object or sample. These waves are referred to as OCT interference signals, or simply as interference signals. A computer produces images of two-dimensional cross sections or three-dimensional volume renderings of the sample by using information on how the waves are changed upon reflection. Spectral Domain OCT and Swept Source OCT systems differ, however, in the type of optical source that they each utilize and how the interference signals are detected.

Spectral Domain OCT systems use a broadband optical source and a spectrally resolving detector system to determine the different spectral components in a single axial scan ("A-scan") of the sample. Thus, spectral Domain OCT systems usually decode the spectral components of an interference signal by spatial separation. As a result, the detector system is typically complex, as it must detect the wavelengths of all optical signals in the scan range simultaneously, and then convert them to a corresponding interference dataset. This affects the speed and performance of Spectral Domain OCT systems.

In contrast, Swept Source OCT systems encode spectral components in time, not by spatial separation. Swept Source OCT systems typically utilize wavelength (frequency) swept sources that "sweep" in the scan range. The interference signals are then typically detected by a non-spectrally resolving detector or specifically a balanced detector system.

Compared to Spectral Domain OCT technology, Swept Source OCT often does not suffer from inherent sensitivity degradation at longer imaging depths, provides faster scanning speed and improved signal to noise ratio ("SNR"), and reduces the complexity of the detector system.

Despite the advantages of Swept Source OCT, certain problems exist. For example, large amounts of memory and processing power are required for resampling algorithms that include Fast Fourier Transforms (FFT), especially when real-time processing is desired. Selection of FFTs typically involves a cost tradeoff between core size/number of FFT points and the time required to perform the transform, also known as the transform time. The transform time increases with increasing interference dataset width. As a result, operators typically purchase different versions of the OCT equipment in response to their signal processing needs and dataset width, which increases cost. The processing burden of the computer systems that perform the resampling increases as the number of sample points generated per scan of the sample increases. The performance of general purpose processors is insufficient for the needs of real-time OCT data acquisition and imaging.

SUMMARY

The present invention involves mathematically resampling signals within an FPGA-based data acquisition board based on data sampled from a wide free spectral range reference interferometer. The FPGA can then multiply up the reference clock rate to achieve greater imaging depth. The Nyquist fold-over depth can thus be programmed from a standard reference to an arbitrary depth, much as PLL frequency synthesizer can produce many frequencies from a standard stable reference. The system is also capable of real-time performance.

The invention provides an optical coherence analysis system that implements a field programmable gate array (FPGA) to multiply a signal to synthesize a higher frequency signal, which achieves an effectively greater-depth virtual clock. The FPGA can further resample a signal in real time with minimal sweep latency.

In certain aspects, the invention provides a system for resampling an optical coherence tomography signal. The system includes a frequency scanning light source for generating a swept optical signal and a k-clock module that generates a reference signal in response to frequency sweeping of the swept optical signal. The system also includes an interferometer that generates interference signals from the swept optical signal. The system further includes a data acquisition module (DAQ) configured to sample the reference signal at a constant rate and resample the reference signal at uniform optical frequency intervals and a field programmable gate array (FPGA) configured to multiply the reference signal.

In certain embodiments, the frequency scanning light source is a tunable laser. The signals may be sampled at 500 MS/s or faster.

The DAQ may further include an analog-to-digital converter for performing hardware-based sample clocking. The FPGA may be further configured to acquire a B-scan and to deliver an image. Delivering an image may include one or more of: FFT processing; logarithmic compression; gray scaling; JPEG compression; and real-time delivery of images.

The FPGA may be configured to reduce harmonic distortion in the signal via direct convolution with finite impulse response digital filters. It may also be configured to measure a phase of the signal. The phase may be multiplied by a programmable register value, thereby increasing the virtual clock depth. A resampling event may be triggered by the multiplied phase crossing an integer boundary.

In related aspects, the invention provides a method for resampling an optical coherence tomography signal. The method involves generating a swept optical signal using a frequency scanning light source and generating a reference signal with a k-clock module in response to frequency sweeping of the swept optical signal. The method further involves generating an interference signal from the swept optical signal with an interferometer. The method further involves sampling the reference signal at a constant rate with a data acquisition module (DAQ) and resampling the reference signal at uniform optical frequency intervals with the DAQ. The method also involves multiplying the reference signal with a field programmable gate array (FPGA).

In certain embodiments, the frequency scanning light source is a tunable laser. The signal may be sampled at 500 MS/s or faster.

In some embodiments, the method involves performing hardware-based sample clocking with an analog-to-digital converter. The method may further involve using the FPGA to acquire a B-scan and deliver an image. Delivering an image may include one or more of: FFT processing; logarithmic compression; gray scaling; JPEG compression; and real-time delivery of images.

The method may further involve using the FPGA to reduce harmonic distortion in the signal via direct convolution with finite impulse response digital filters or using the FPGA to measure a phase of the signal. The phase may be multiplied by a programmable register value that increases the virtual clock depth. A resampling event may be triggered by the multiplied phase crossing an integer boundary.

BRIEF DESCRIPTION OF THE DRAWINGS

FIG. 8 shows additional parameters of the demonstration of FIGS. 3A-3C.

DETAILED DESCRIPTION

Figure 1:
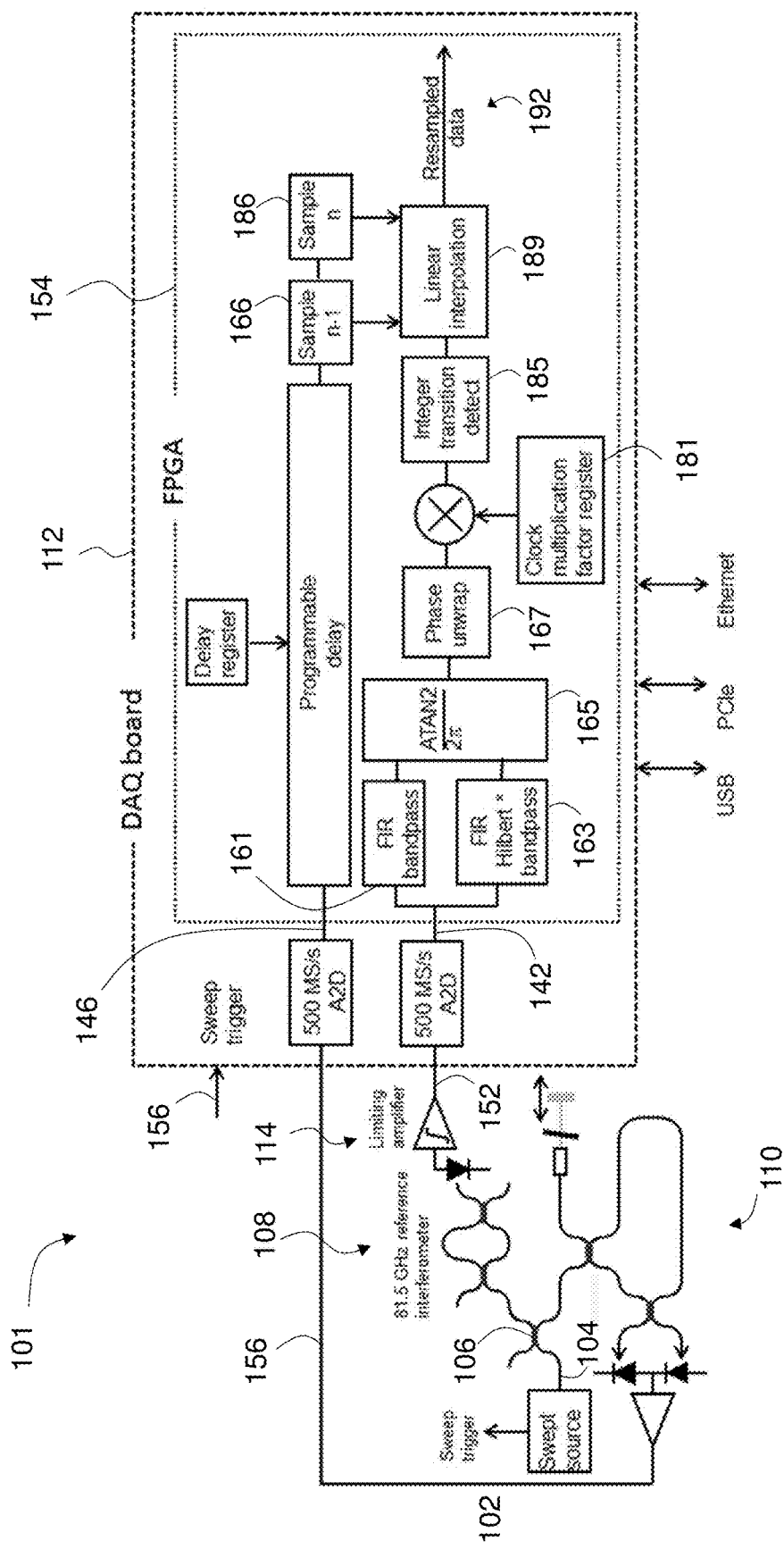
FIG. 1 shows a schematic diagram of an optical coherence analysis system.

The invention relates to swept source OCT systems. Swept Source OCT systems can use a sampling clock, or k-clock, for sampling (including resampling) the interference signals. The k-clock may be generated by a k-clock module that generates a signal that indicates every time the swept source tunes through a predetermined frequency increment of the scan band. The k-clock is used to correct for non-linearity in the frequency sweeping of the swept source.

Some Swept Source OCT systems use a hardware-based k-clocking to directly clock the Analog-to-Digital ("A/D") converter of a Data Acquisition ("DAQ") system for sampling the interference signals. Other Swept Source OCT systems use software-based k-clocking, wherein the k-clock signals are sampled from the k-clock module in the same manner as the interference signal, creating a k-clock dataset of all sampled k-clock signals and an interference dataset of all sampled interference signals. Then, the k-clock dataset is used to resample the interference dataset. The resampling provides data that are evenly spaced in the optical frequency domain, or k-space. This provides maximal SNR and axial imaging resolution for subsequent Fourier transform-based signal processing upon the acquired interference signal spectra or interference dataset.

Swept Source OCT systems require resampling or k-clock control of the interference sampling to compensate for instability and/or non-linearity in the tuning of the swept sources in frequency. The use of the k-clock yields interference data that are evenly spaced in the optical frequency domain, or k-space, which provides maximal signal-to-noise ratio (SNR) and axial imaging resolution for subsequent Fourier transform-based signal processing upon the acquired interference signal spectra, or interference dataset. The Fourier transform provides the "A-scan" information, or axial scan depth profile within the sample.

OCT systems are known in the art, including those described in U.S. Patent Publications 2015/0184995, filed Dec. 30, 2013; 2009/0290167, filed Mar. 2, 2009; and 2011/0080591, filed Oct. 2, 2009, the contents of each of which is incorporated by reference in its entirety.

OCT systems typically resample their interference datasets using linear phase information extracted from the k-clock dataset. Because the linear phase information is evenly spaced in k-space, it can be utilized as a resampling clock. Typically, OCT systems extract the linear phase information from the k-clock dataset using a Hilbert Transform.

Hilbert Transforms utilize multiple FFT-based computations. As a result, the Hilbert transform-based process of extracting phase information from the k-clock dataset typically introduces two additional FFT computations or stages. When combined with the processing associated with the final FFT stage for creating the A-lines from the linearized interference dataset, current OCT systems and methods have poor real-time performance.

The present invention employs a data acquisition (DAQ) board including a field programmable gate array (FPGA) to sample and resample a signal. The FPGA implements filters for converting the k-clock dataset into a reconstructed k-clock dataset. The system spectrally filters the k-clock dataset with a bandpass filter and a Hilbert transform bandpass filter.

The resampling step typically required in optical coherence tomography (OCT) to linearize the sweep in optical frequency can be done by direct hardware k-clocking, or mathematically on a computer, GPU, or FPGA. See, e.g., Choma et al., 2005, "Swept source optical coherence tomography using an all-fiber 1300-nm ring laser source," Journal of Biomedical Optics 10(4):4400; Zhang & Kang, 2010, "Graphics processing unit accelerated non-uniform fast Fourier transform for ultrahigh-speed, real-time Fourier-domain OCT," Optics Express 18(22):23472-87; Desjardins et al., 2009, "Real-time FPGA processing for high-speed optical frequency domain imaging," IEEE Transactions on Medical Imaging 28(9):1468-72; and Bandi et al., 2013, "FPGA-based real-time swept-source OCT systems for B-scan live-streaming or volumetric imaging," Proceedings of SPIE 8571, Optical Coherence Tomography and Coherence Domain Optical Methods in Biomedicine XVII, 85712Z (6 pages), the entire contents of each of which is incorporated by reference.

The present invention uses a field programmable gate array (FPGA) implementation where a coarse k-clock or reference interferometer signal (i.e., a signal having a wide free spectral range (FSR) and low depth) is multiplied up mathematically. FPGAs have previously been used in OCT analysis. See Li et al., "Scalable, High Performance Fourier Domain Optical Coherence Tomography: Why FPGAs and Not GPGPUs," Proceedings of the 2011 IEEE 19th Annual International Symposium on Field-Programmable Custom Computing Machines, FCCM '11, 2011, the entire contents of which are incorporated by reference. Prior art approaches have instead multiplied the signal to synthesize a higher frequency signal. The mathematical approach of the present invention achieves an effectively deeper depth virtual clock.

The mathematical approach of the present invention provides numerous benefits. This FPGA-based approach to resampling will enable new real-time imaging and phase-sensitive applications. It will allow both more standardization of hardware and more flexibility of application. For example, it provides a standardized clock interferometer, which can be used to fit all applications. Typically, the reference interferometer will be shorter than the Nyquist depth.

Additionally, the present invention allows changing the Nyquist depth in software. Non-integer multiplication factors can be used. The process is similar to synthesizing arbitrary frequencies from a reference in a phase locked loop (PLL). The present system is useful with variable sweep rate lasers, allowing both fast/shallow and slow/deep imaging modes to be available in one system.

The clock interferometer can double as a wavelength reference or trigger. That is useful for phase-sensitive applications. In some embodiments, stabilized reference interferometers or triggers can be implemented for long-term stability.

The mathematical multiplying approach can also generate a high quality large depth virtual clock in cases where coherence length is limited. The FPGA of the present system can implement relative delay matching between clock and signal. The shift register length can be programmed with a time resolution of a fixed-frequency sample interval. Resampling can occur in real time with latency of less than 1 sweep.

The FPGA of the present system can be used for further image processing, including FFT processing, logarithmic compression, gray scaling, JPEG compression, and real-time delivery of the images, such as over a 1G Ethernet link.

FIG. 1 shows a schematic diagram of an optical coherence analysis system 100 configured for FPGA resampling according to the present invention. The data acquisition board (DAQ) 112 samples the signal and reference interferometer data at a constant 500 MS/s rate or faster and resamples the signal at uniform optical frequency intervals.

The OCT system 100 uses a swept source 102 to generate swept optical signals on optical fiber 104. The swept source 102 is typically a tunable laser designed for high speed spectral sweeping. The swept optical signals are narrowband emissions that are scanned, or "swept," over a spectral scan band. Tunable lasers are constructed from a gain element such as a semiconductor optical amplifier ("SOA") that is located within a resonant laser cavity, and a tuning element such as a rotating grating, a grating with a rotating mirror, or a Fabry-Perot tunable filter. Tunable lasers are known in the art, such as those described in U.S. Pat. Nos. 7,415,049 and 8,526,472, incorporated herein by reference in its entirety.

A fiber coupler 106 or other optical splitter divides the swept optical signal from the swept source 102 into a portion that is provided to an OCT interferometer 108 and a portion that is provided to a k-clock module 110 for generating a reference signal. A controller (not shown) controls the swept source 102 and the DAQ 112.

The interferometer 108 may be, for example, a Mach-Zehnder-type that sends optical signals to a sample, analyzes the optical signals reflected from the sample, and generates an optical interference signal in response.

The k-clock module 110 generates optical k-clock signals at equally spaced optical frequency sampling intervals as the swept optical signal is tuned or swept over the scan band. The optical k-clock signals are converted into electronic k-clock signals 156, which are used by the data acquisition system 112 to track the frequency tuning of the optical swept source 102.

There are a number of ways to implement the k-clock module 110. One example utilizes a Michelson interferometer. These generate a sinusoidal response to the frequency scanning of the swept optical signal. In specific implementations, a fiber Michelson interferometer is used. In other implementations, etalons are used in the k-clock module to filter the swept optical signal. An example of a clock integrated with a swept source laser is described in U.S. Pat. No. 8,564,783, incorporated by reference in its entirety.

The DAQ 112 accepts the electronic interference signals 152 and the electronic k-clock signals 156. The DAQ 112 accepts a sweep trigger signal 158 indicating the start of the sweeps of the swept source 102. In the embodiment shown, signals 156 and 152 are sampled at 500 MS/s to generate a k-clock dataset 146 and an interference dataset 142, respectively. The DAQ 112 includes an FPGA 154 that implements resampling algorithms for resampling of the interference dataset 142.

The resampling algorithm used in the FPGA 154 is different than what is typically done offline on a computer. On a computer, block FFT methods are usually used for the bandpass filters and Hilbert transform. On the FPGA 154, these steps are done by direct convolution with FIR digital filters 161 and 163. The bandpass step cuts the harmonic content from the reference interferometer since it has a limiting amplifier that squares up the reference signal. That is followed by a phase measurement system including an ATAN2 calculation 165 and phase unwrapping 167.

The phase is multiplied by a programmable register value 181 that typically is set to increase the virtual clock depth. Finally, at the integer transition detection unit 185 when the multiplied phase crosses an integer boundary, it triggers a resample event. The resampled data 192 is formed by linear interpolation 189 between two adjacent fixed frequency samples 166 and 186. The fixed frequency samples 166 and 186 are spaced by, for example, 2 nanoseconds (ns).

The DAQ 112 is preferably included as part of a computer system (not shown). The controller may accept commands from software running on the computer system to control components of the OCT system 100. In addition to hardware k-clocking, the DAQ is capable of acquiring B-scans and delivered full images from the FPGA. This included FFT processing, logarithmic compression, gray scaling, JPEG compression, and real-time delivery of the images over a 1G Ethernet link. In some embodiments, the system 100 is coupled to a display device (not shown) for displaying information about the system 100 and its components to an operator. The computer system may store in a non-transitory memory data related to scanning of the sample.

Figure 2:
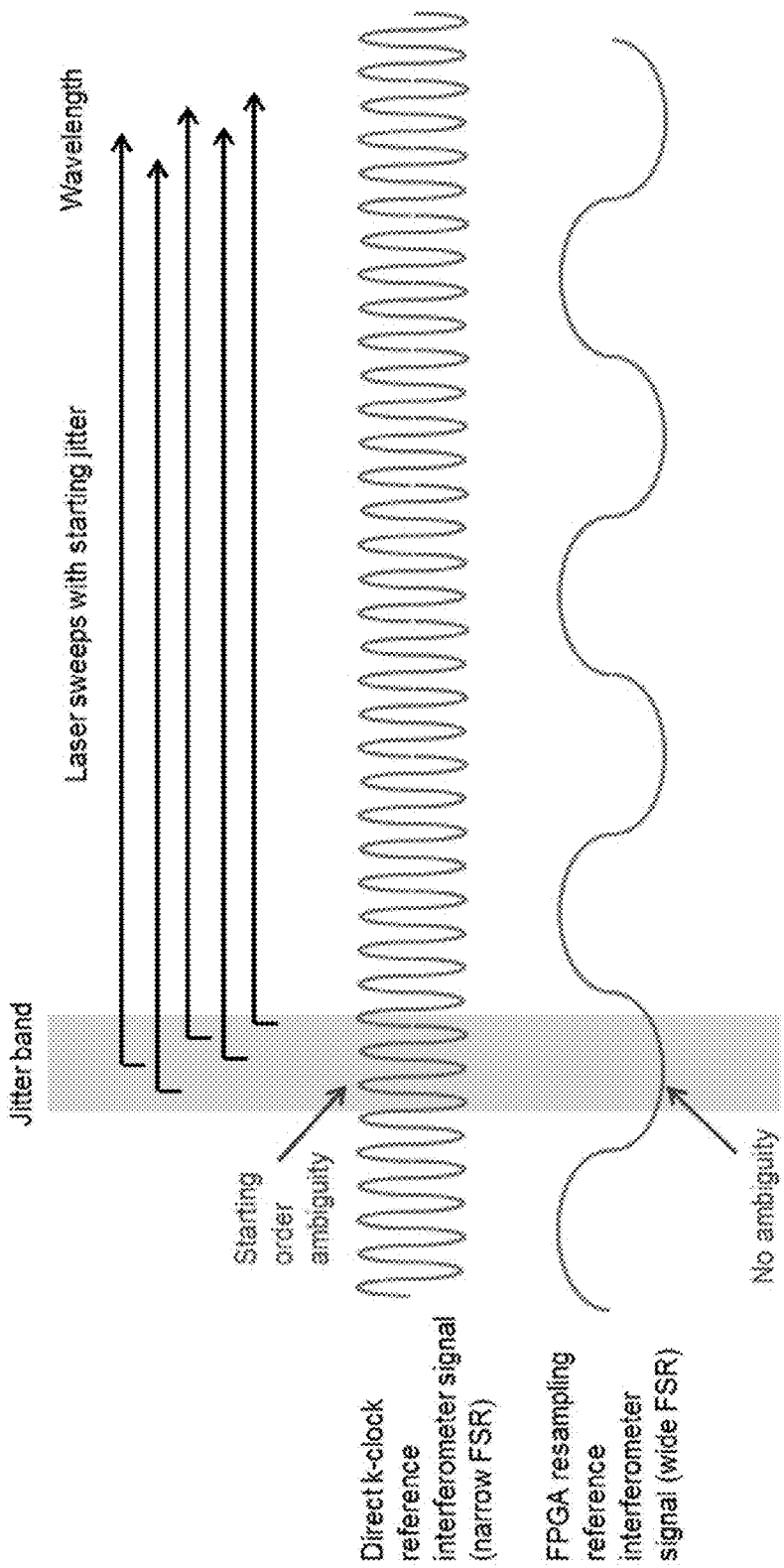
FIG. 2 shows wavelength sweeps with jitter and a narrow FSR reference filter required for direct hardware k-clock and wide FSR filter used with FPGA resampling

Many swept lasers have jitter in their starting wavelengths that make phase-sensitive OCT applications more difficult. A system with a wavelength trigger, for example a Bragg grating, can compensate for this by measuring when the laser sweeps by the starting wavelength. A narrow FSR interferometer cannot serve this purpose because of starting order uncertainty. FIG. 2 shows wavelength sweeps with jitter and a narrow FSR reference filter required for direct hardware k-clock (top) and wide FSR filter used with FPGA resampling. FPGA resampling will allow the reference interferometer to be also used as a wavelength trigger because it can have a wide FSR, but still be multiplied up to the equivalent of a narrow FSR reference. For more information, see Vakoc et al., 2005, "Phase-resolved optical frequency domain imaging," Optics Express 13(14):5483-93.

Figure 3:
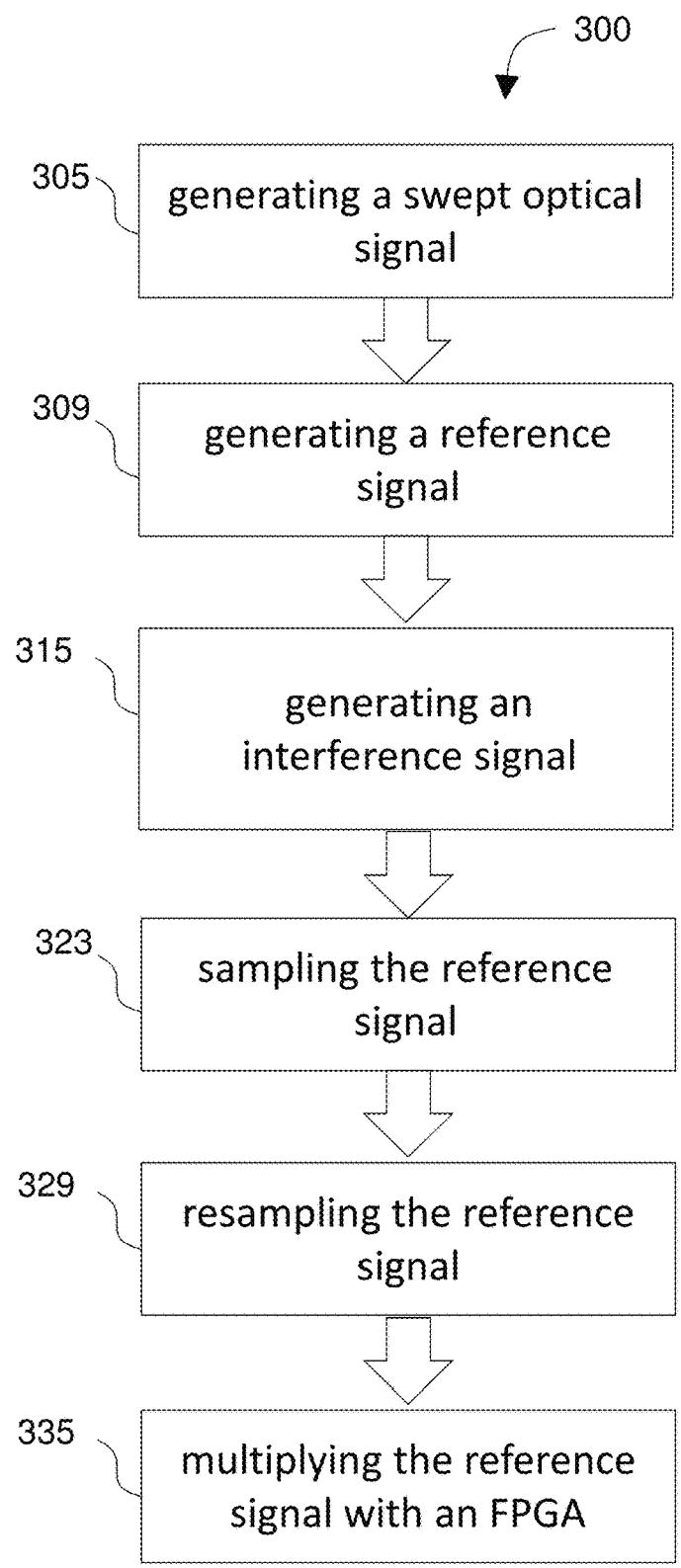
FIG. 3 shows a method of the invention.

FIG. 3 shows a method 300 for resampling an optical coherence tomography signal according to the present invention. The method 300 involves generating a swept optical signal 305 using a frequency scanning light source. The method also involves generating a reference signal 309 with a k-clock module in response to frequency sweeping of the swept optical signal. The method 300 further involves generating an interference signal 315 from the swept optical signal with an interferometer. The method 300 further involves sampling the reference signal 323 at a constant rate with a data acquisition module (DAQ) and resampling the reference signal 329 at uniform optical frequency intervals with the DAQ. The method also involves multiplying the reference signal 335 with a field programmable gate array (FPGA).

EXAMPLE

The following example and corresponding figures demonstrate the use of the OCT system of the present invention. Point-spread data and images were resampled using the system and method described herein, using a 100 nm sweep from a 1060 nm, 100 kHz swept source. An 81.5 GHz free spectral range (FSR) reference interferometer was multiplied 3.81 times to achieve a 3.5 mm Nyquist depth. Shot noise limited sensitivity and transform limited point spread widths were achieved.

As implemented, there were sideband artifacts from the linear interpolation step. Simulations show that the problem can be eliminated by switching to a band-limited interpolation algorithm.

Figure 4A:
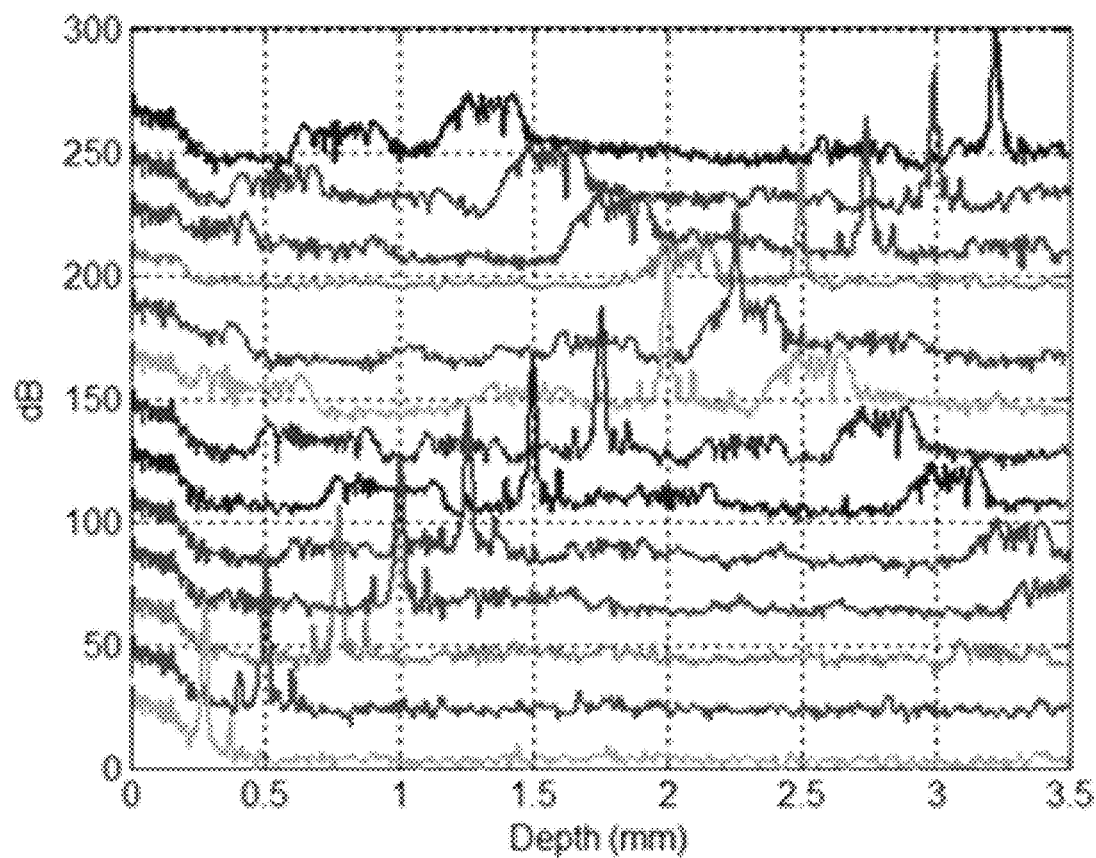
FIGS. 4A-4C show experimental point spread measurements using FPGA resampling (FIG. 4A), simulation of resampling using linear interpolation (FIG. 4B), and simulation of resampling using a more advanced band-limited resampling technique (FIG. 4C)
Figure 4B:
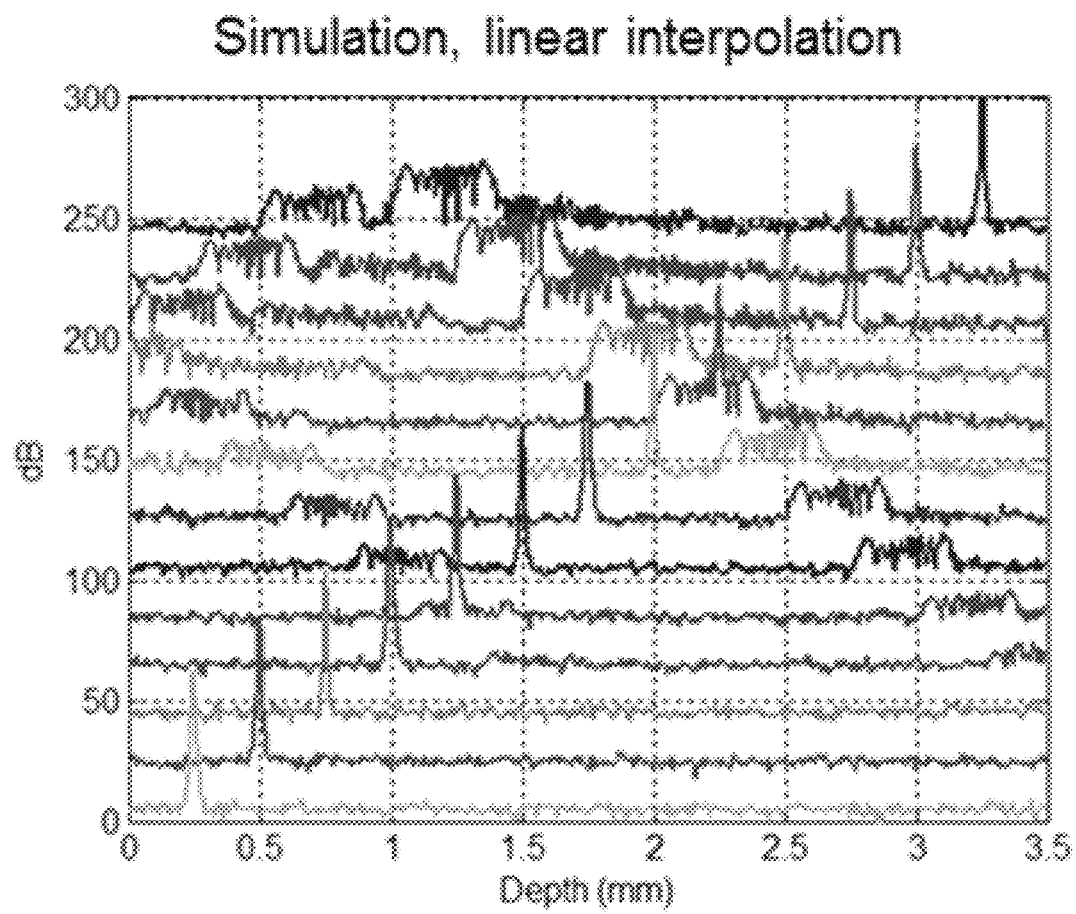
Figure 4C:
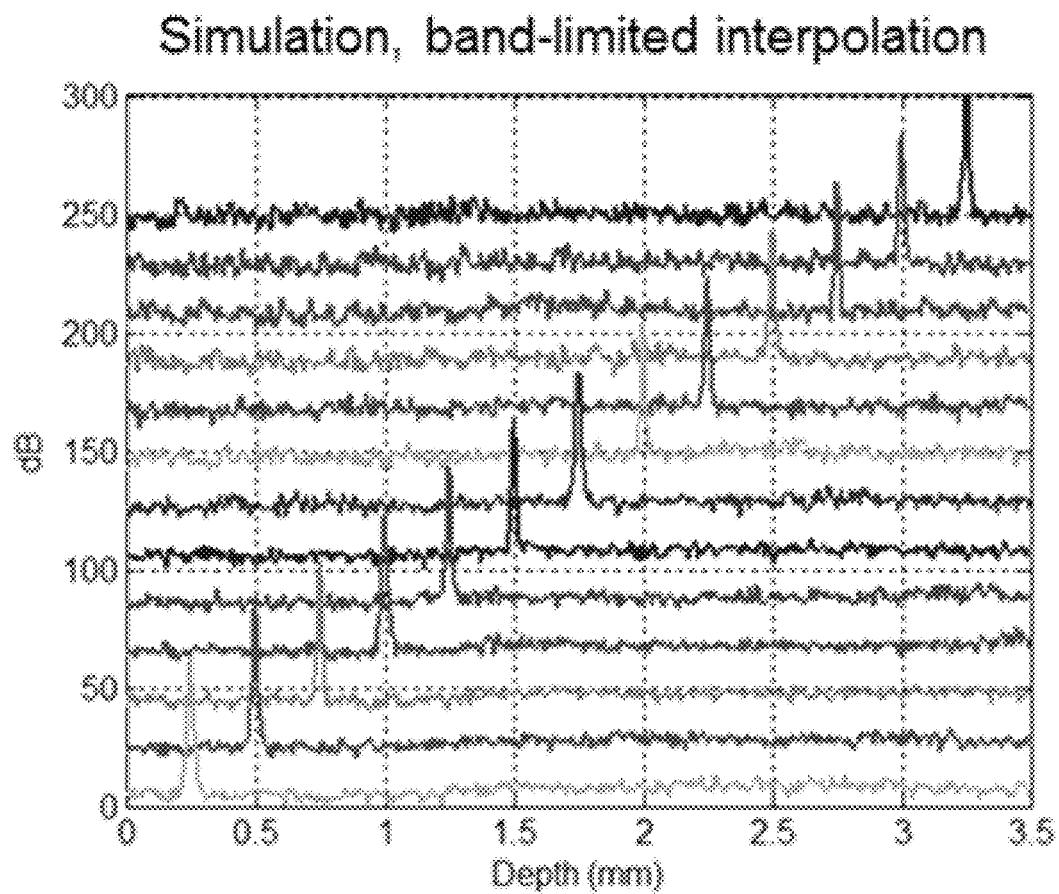

FIGS. 4A-4C show experimental point spread measurements using FPGA resampling (FIG. 4A), simulation of resampling using linear interpolation (FIG. 4B), and simulation of resampling using a more advanced band-limited resampling technique (FIG. 4C). Resampled data was read and dispersion corrected. The data in FIGS. 4A-4C represent ten averaged traces. Shot-noise limited sensitivity (106 dB for 2.1 mW signal power) and transform limited point spread widths (within 10% of the Hann window limit at 3, 10 and 20 dB from peak) were obtained. The main drawback of the method as implemented in this example is the sideband artifacts that increase with depth. That is caused by the linear interpolation step, and is seen in both the experimental results (FIG. 4A) and the simulation (FIG. 4B). That issue can be resolved by bandlimited interpolation algorithm, as simulated in FIG. 4C.

Since the system can simultaneously have a deep Nyquist depth and a wide FSR reference interferometer, the interferometer can serve both as a wavelength trigger and k-clock reference. If the FSR is much wider than the sweep-to-sweep laser wavelength jitter, there will be no order ambiguity and the sampling can always start at the same clock phase. This would create a phase stable system. Long term stability could be achieved if the reference interferometer was environmentally (e.g., temperature) controlled.

Figure 5:
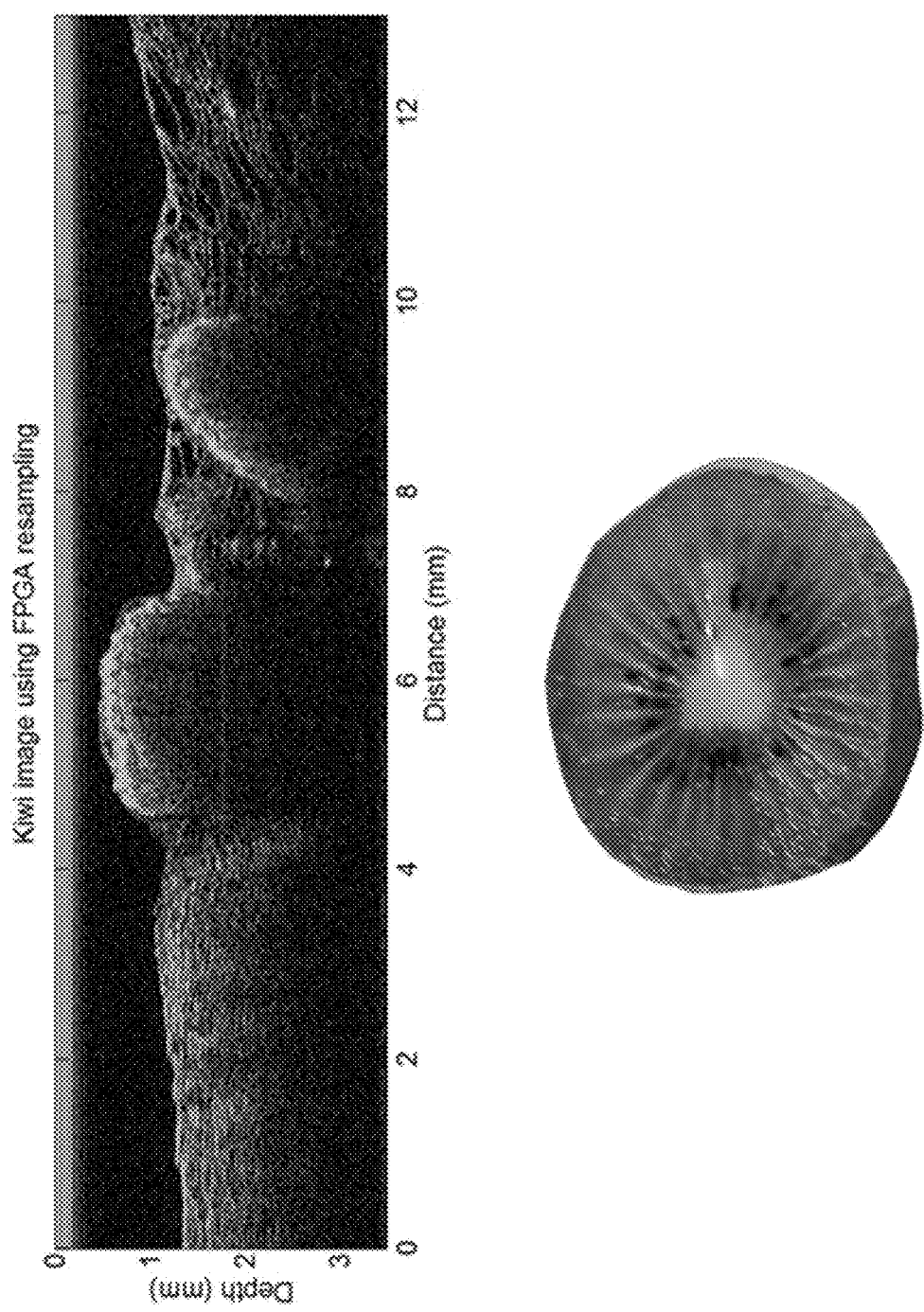
FIG. 5 shows an example OCT image obtained using systems of the invention.

Despite the artifacts from linear interpolation, quality OCT images can be obtained, as shown in FIG. 5, which shows an image of a kiwi slice using FPGA resampling of the present invention.

Figure 6:
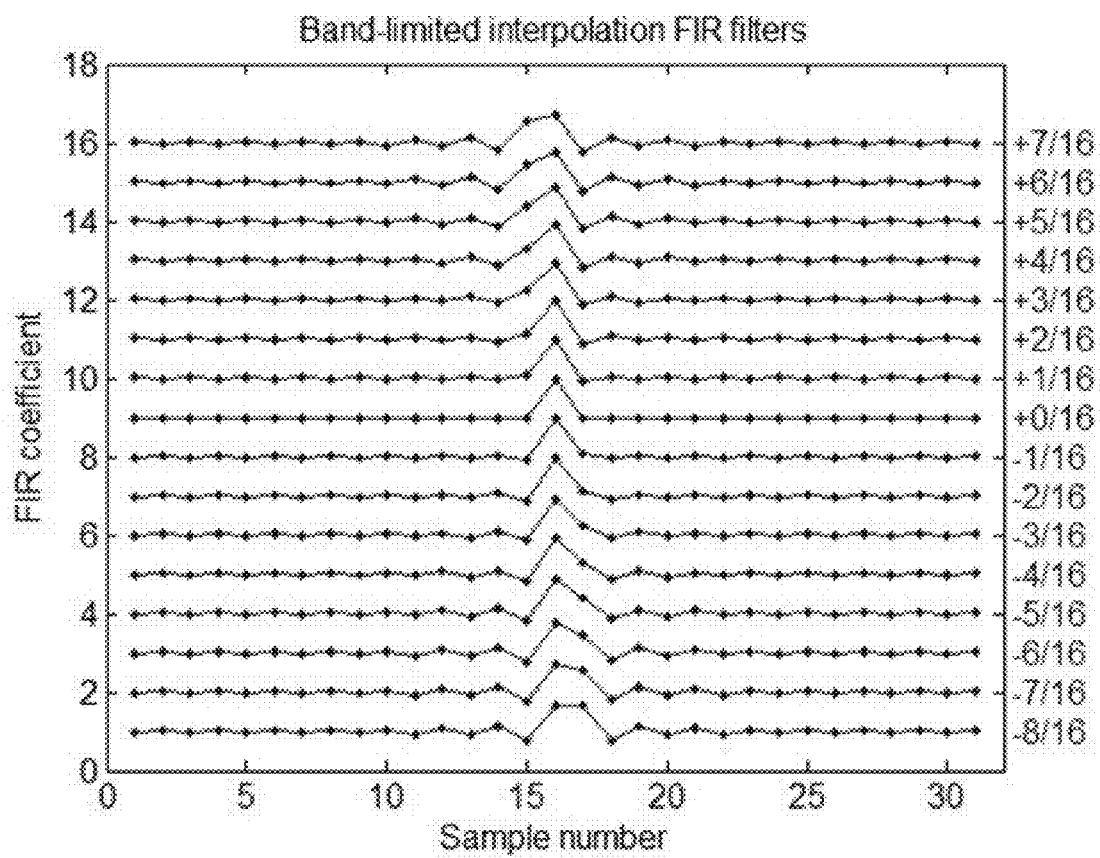
FIG. 6 shows an example bank of FIR filters that can be used for band-limited resampling.

As noted above, there are artifacts associated with simple linear interpolation, and band-limited interpolation can provide superior performance. The example (FIG. 4C) was calculated using the set of truncated FIR sinc( ) filters in FIG. 6. FIG. 6 shows an example bank of 16 FIR filters that could be used for band-limited resampling. These filters are convolved with raw input samples (500 MS/s samples in this demonstration/example). The outputs of these filters subdivide the input into 16 divisions for an effective 16×500 MS/s sampling rate. Interpolation involves picking the appropriate one of 16 in the resampling step, or possibly interpolating between adjacent ones. In this example, the filters have 31 taps. The number of taps and number of subdivision is variable, depending on required performance. There are other, similar, filters to the truncated sinc( ) that serve the same purpose that could be implemented by similar means. See, e.g., Laakso et al., 1996, "Splitting the Unit Delay—Tools for Fractional Delay Filter Design," IEEE Signal Processing Magazine 13:30-60, incorporated by reference in its entirety.

Figure 7:
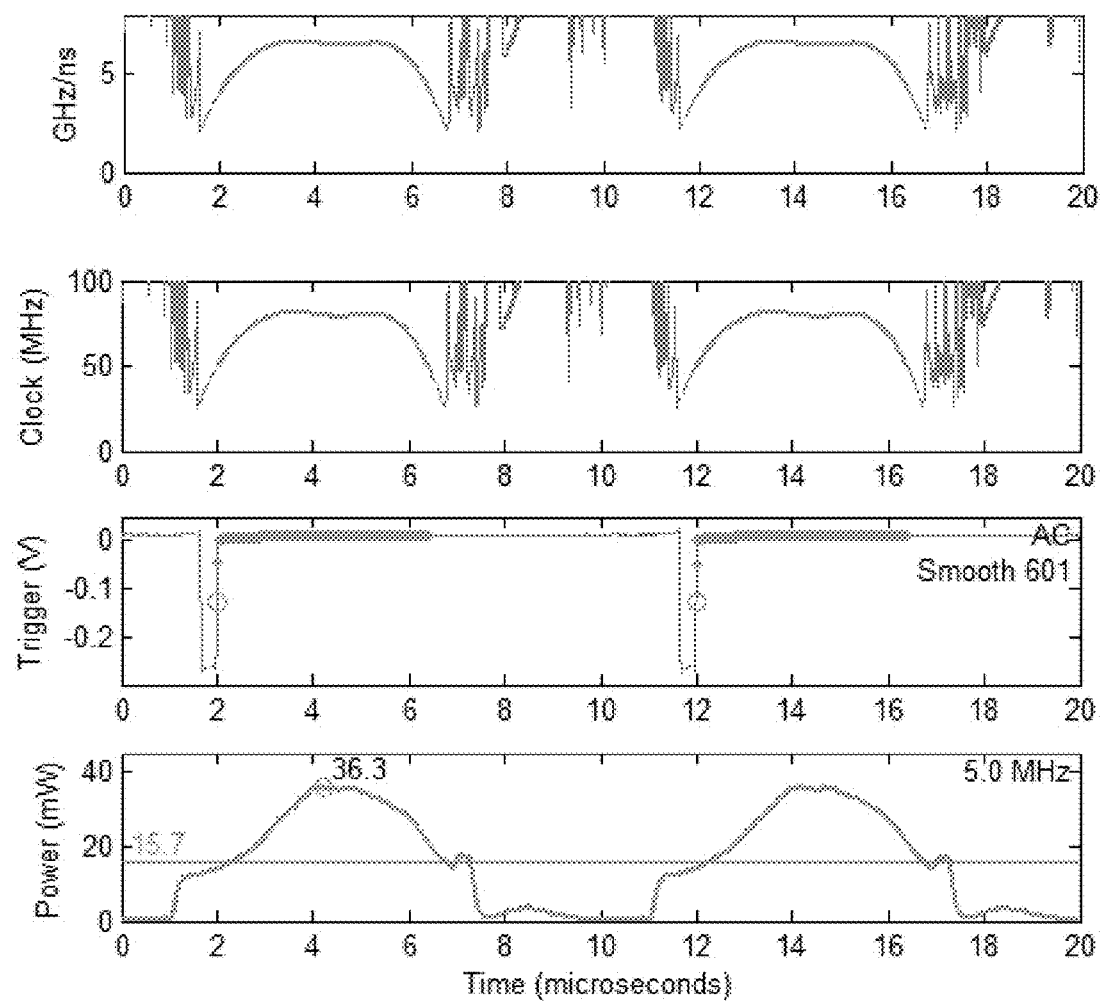
FIG. 7 shows data for the swept laser demonstration of FIGS. 3A-3C.

FIG. 7 shows data for the swept laser used in the demonstration described above, with additional parameters listed in FIG. 8. FIG. 7 shows swept laser waveforms including sweep rate, clock frequency, trigger points, and power output. The laser sweeps short to long wavelength starting at the rising trigger pulse. The optical sweep rate, in GHz/ns, is not constant across the sweep, which is why there is need for FPGA resampling/linearization. The reference clock frequency is the sweep rate divided by the 81.5 GHz free spectral range (FSR) of the reference interferometer. The optical power output of the laser is shown in the final plot.

Figure 9:
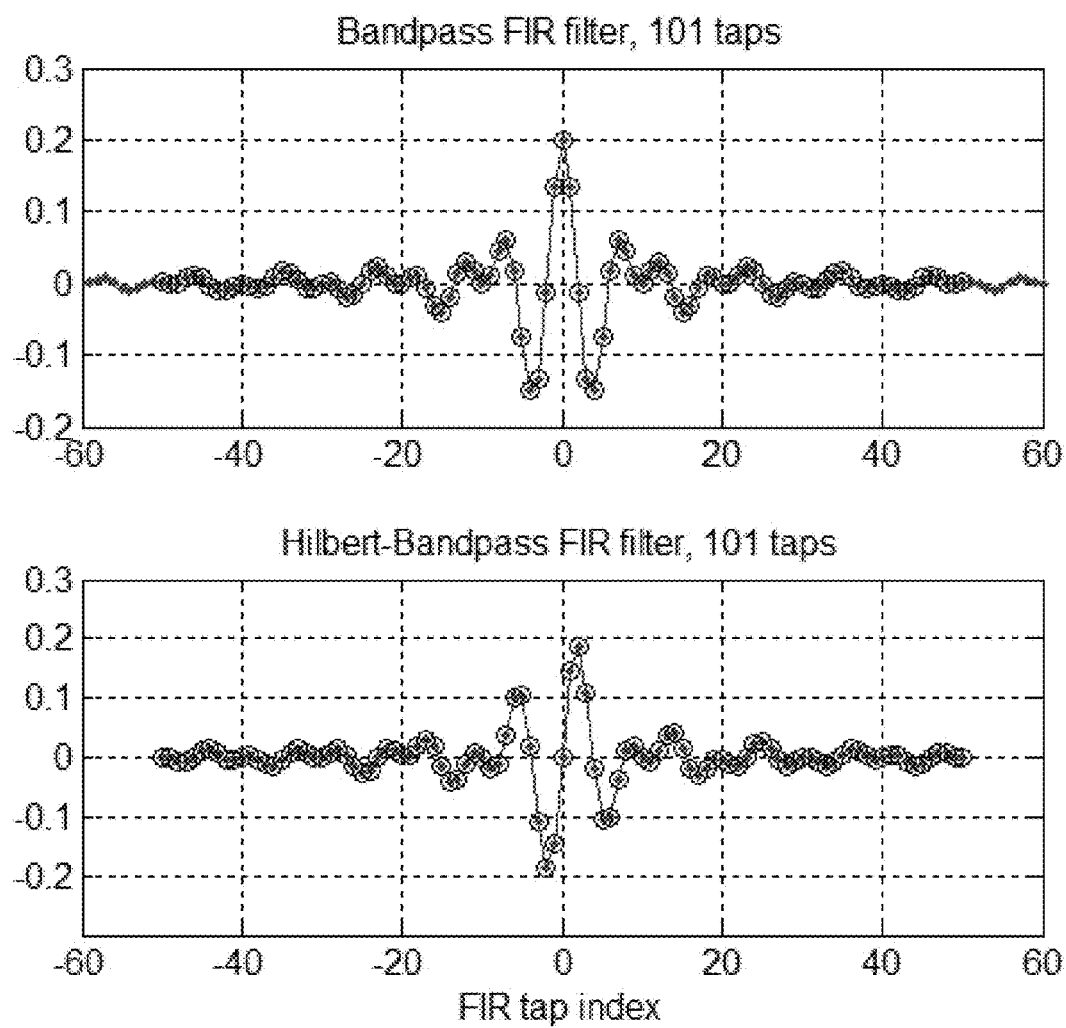
FIG. 9 shows sample FIR filter impulse responses for a 40-90 MHz passband.
Figure 10:
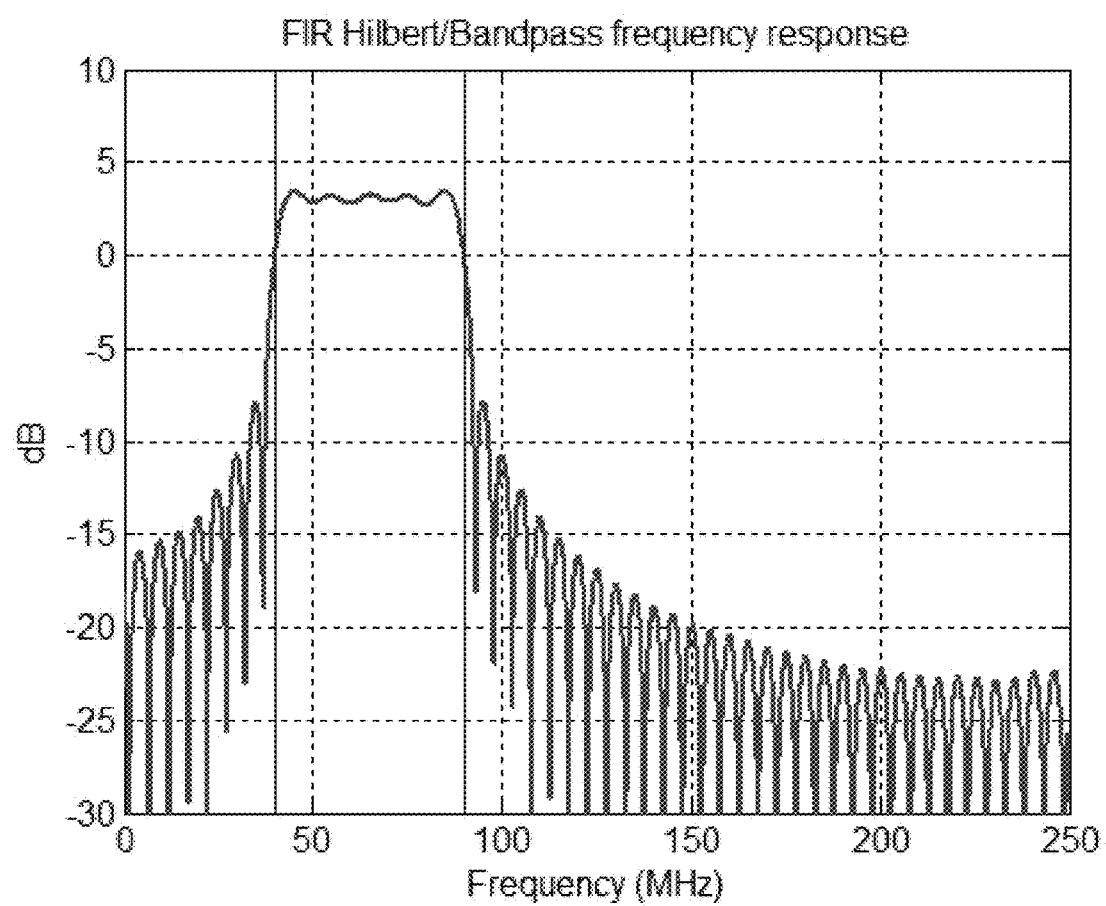
FIG. 10 shows the calculated frequency response of the FIR filter of FIG. 8.

The reference interferometer frequency range is 50 to 80 MHz in this demonstration. The Finite Impulse Response (FIR) digital bandpass and bandpass-Hilbert filters need to be configured for this range. FIG. 9 shows the 101-tap FIR filter impulse responses (bandpass FIR filter on top, and Hilbert-bandpass FIR filter on bottom) for a 40-90 MHz passband. The calculated frequency response of the FIR filter is shown in FIG. 10.

Figure 11:
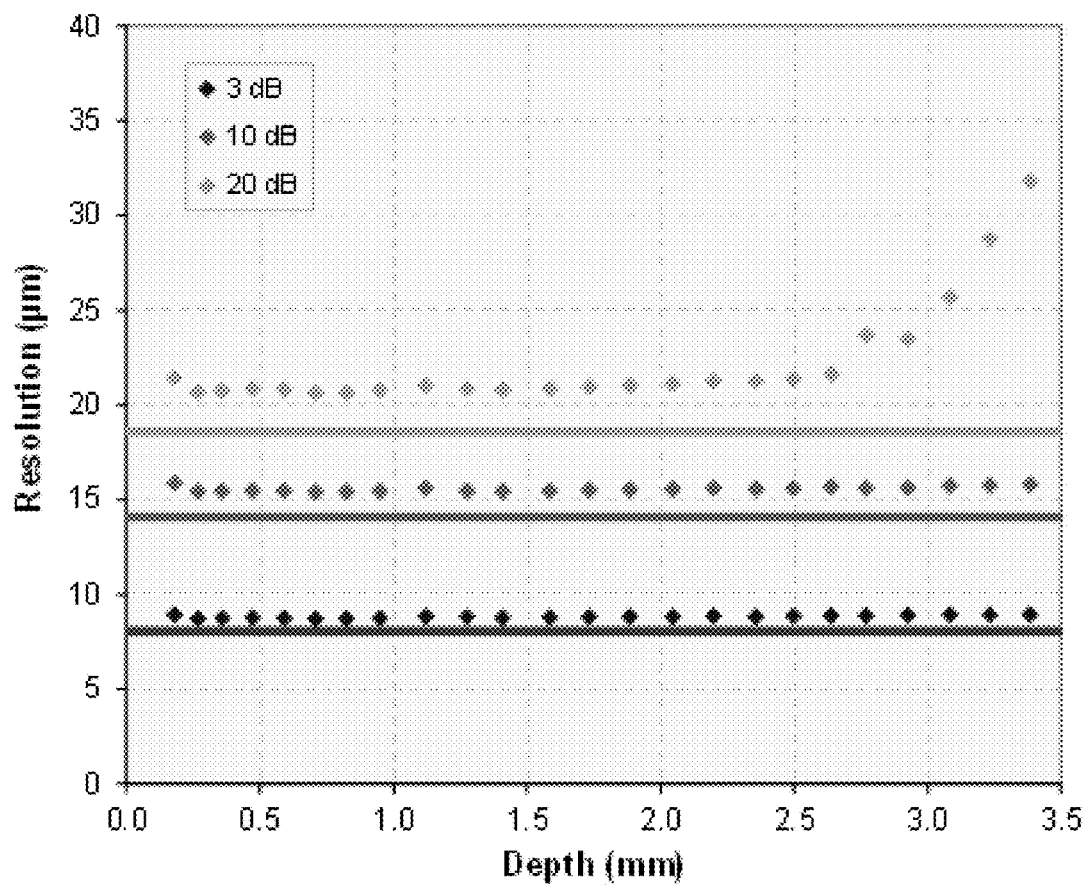
FIG. 11 shows experimental results comparing system resolution measurements with the theoretical limits for Hann window processing.

A key metric of resampling performance is the point spread width of the OCT system. To determine if it could achieve the theoretical resolution limit as shown in the table in FIG. 8, the resolution was measured and calculated using a Hann window in the FFT processing step for making the OCT image. FIG. 11 shows the results comparing system resolution measurements with the theoretical limits for Hann window processing. The dots are measurements and the lines are the limits listed in FIG. 8. The data are for the widths 3, 10, and 20 dB below the point spread peak.

One the advantages of the FPGA resampling implementation is that signal/clock relative delay can be coded into the FPGA using variable delay shift registers, shown in the system diagram of FIG. 1. There are two programmable shifts, one for the signal and one for the clock, so the signal can be shifted positively or negatively relative to the clock using the two shift registers which can only delay. This is important flexibility since an OCT systems have different amounts of optical fiber and electronic delays.

Figure 12:
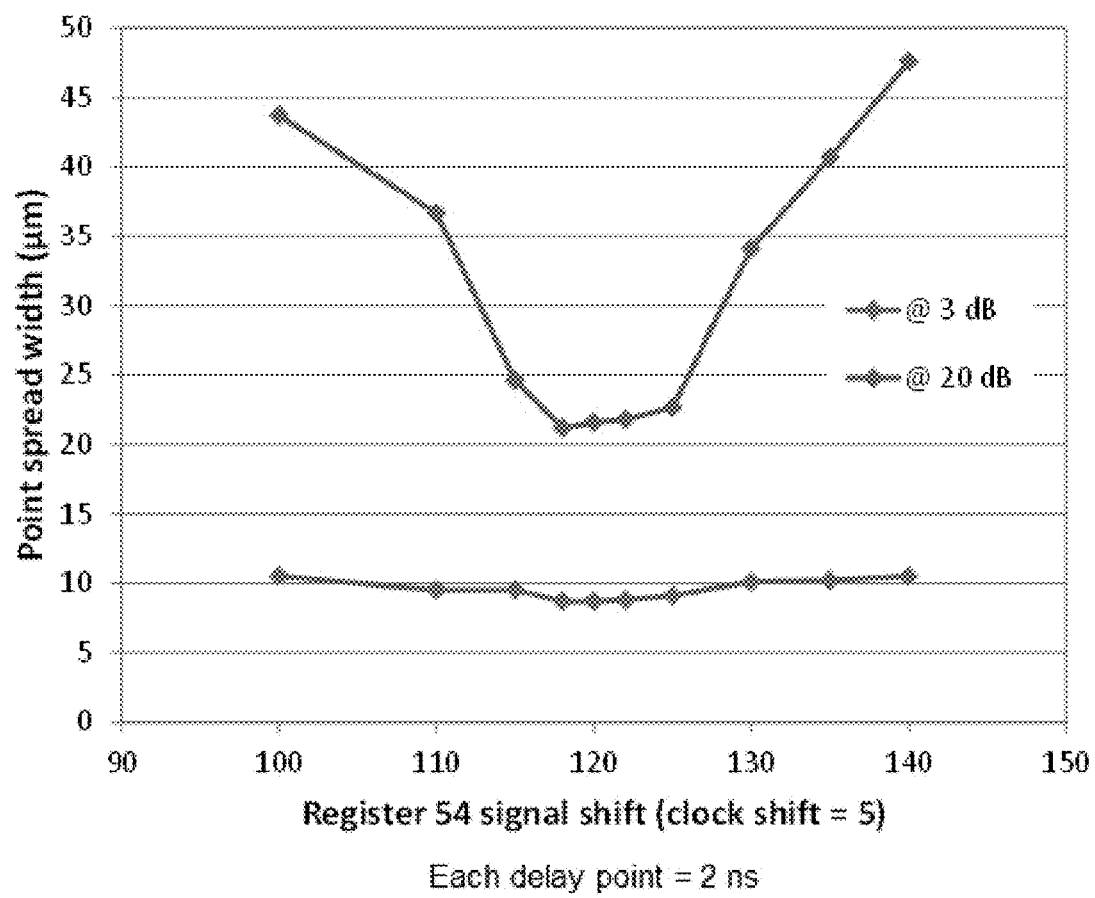
FIG. 12 is a graph of sample data showing resolution measurements versus signal shift register value.

Delays have to be fine-tuned for optimal performance, as seen in FIG. 12. FIG. 12 shows resolution measurements versus signal shift register value. Each increment corresponds to a 2-nanosecond delay because the sampling rate is 500 MS/s. The OCT system resolution (point spread width) is optimum when all the system delays (optical, electrical, and FPGA) are aligned.

Figure 13:
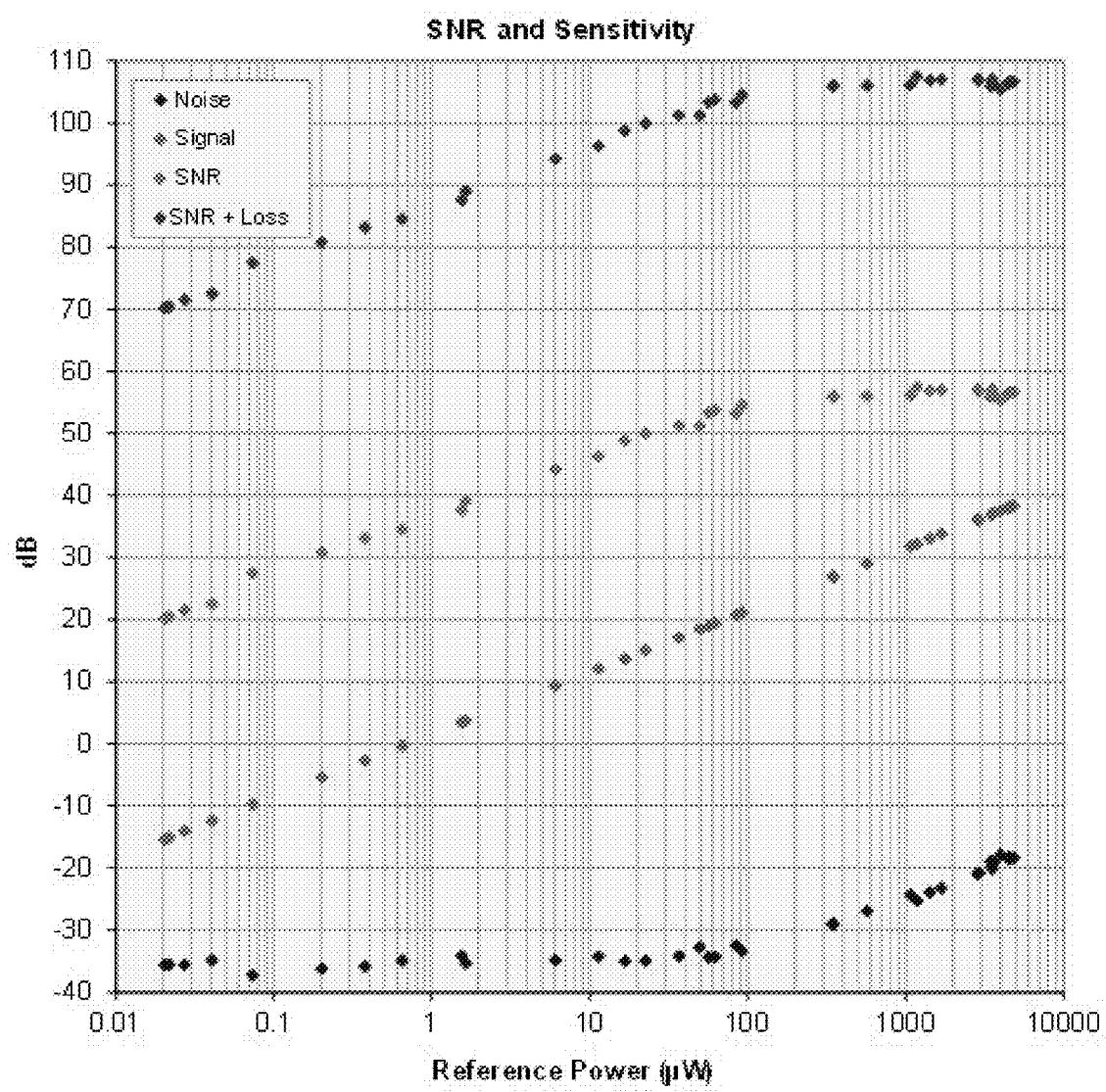
FIG. 13 shows a graph of signal, noise, SNR, and sensitivity versus reference power.

FIG. 13 shows further proof of the quality of the FPGA resampling demonstration. The graph shows signal, noise, SNR, and sensitivity versus reference power. Shot noise limited sensitivity of 106 dB at 2.1 mW signal power was obtained.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A system for resampling an optical coherence tomography signal, the system comprising:
    a frequency scanning light source for generating a swept optical signal;
    a k-clock module that generates a reference signal in response to frequency sweeping of the swept optical signal;
    an interferometer that generates interference signals from the swept optical signal;
    a data acquisition module (DAQ) configured to sample the reference signal at a constant rate and resample the interference signals based on the reference signal at uniform optical frequency intervals; and
    a field programmable gate array (FPGA) of the DAQ configured to multiply the optical frequency intervals to resample the interference signals using bandlimited interpolation.

2. The system of claim 1, wherein the frequency scanning light source is a tunable laser.

3. The system of claim 1, wherein the signals are sampled at 500 MS/s or faster.

4. The system of claim 1, wherein the DAQ comprises an analog-digital converter for performing hardware-based sample clocking.

5. The system of claim 1, wherein the FPGA is further configured to acquire a B-scan and to deliver an image.

6. The system of claim 5, wherein the delivering an image includes one or more from the list comprising: FFT processing; logarithmic compression; gray scaling; JPEG or other type of image compression; and real-time delivery of images.

7. The system of claim 1, wherein the FPGA is configured to reduce harmonic distortion in the signal via direct convolution with finite impulse response digital filters.

8. The system of claim 7, wherein the FPGA is further configured to measure a phase of the signal.

9. The system of claim 8, wherein the phase is multiplied by a programmable register value.

10. The system of claim 9, wherein multiplying increases a virtual clock depth.

11. The system of claim 9; wherein a resampling event is triggered by the multiplied phase crossing an integer boundary.

12. The system of claim 1, wherein a free spectral range of the k-clock module is wider than sweep-to-sweep wavelength jitter of the frequency scanning light source.

13. The system of claim 1, wherein sampling is started at the same clock phase.

14. The system of claim 1, wherein the interpolation is performed using truncated finite impulse response filters.

15. The system of claim 1, wherein bandlimited interpolation is performed using truncated sinc( ) filters.

16. The system of claim 1, wherein the DAQ includes a variable delay, shift register for delaying the interference signals.

17. A method for resampling an optical coherence tomography signal in an optical coherence analysis system, the method comprising:
    generating a swept optical signal using a frequency scanning light source;
    generating a reference signal with a k-clock module in response to frequency sweeping of the swept optical signal;
    generating an interference signal from the swept optical signal with an interferometer;
    sampling the reference signal at a constant rate with a data acquisition module (DAQ);
    resampling the interference signal based on the reference signal at uniform optical frequency intervals with the DAQ; and
    multiplying the optical frequency intervals to resample the interference signal using bandlimited interpolation with a field programmable gate array (FPGA).

18. The method of claim 17, wherein the frequency scanning light source is a tunable laser.

19. The method of claim 17, wherein the signal is sampled at 500 MS/s or faster.

20. The method of claim 17, further comprising performing hardware-based sample clocking with analog-to-digital converter.

21. The method of claim 17, further comprising using the FPGA to acquire a B-scan and deliver an image.

22. The method of claim 21, wherein the delivering an image includes one or more of: FFT processing; logarithmic compression; gray scaling; JPEG or other type of image compression; and real-time delivery of images.

23. The method of claim 17, further comprising using the FPGA to reduce harmonic distortion in the signal via direct convolution with finite impulse response digital filters.

24. The method of claim 23, further comprising using FPGA to measure a phase of the signal.

25. The method of claim 24, wherein the phase is multiplied by a programmable register value.

26. The method of claim 25, wherein multiplying increases the virtual clock depth.

27. The method of claim 25, wherein a resampling event is triggered by the multiplied phase crossing an integer boundary.

28. The method of claim 17, wherein a free spectral range of the k-clock module is wider than sweep-to-sweep wavelength jitter of the frequency scanning light source.

29. The method of claim 17, wherein sampling is started at the same clock phase.

30. The method of claim 17, wherein the bandlimited interpolation is performed using truncated finite impulse response filters.

31. The method of claim 17, wherein the DAQ includes a variable delay shift register for delaying the interference signals.

* * * * *